United States Patent [19]

Nisato et al.

[11] Patent Number: 5,134,124
[45] Date of Patent: Jul. 28, 1992

[54] USE OF A STATIN DERIVATIVE IN THE TREATMENT OF EYE COMPLAINTS

[75] Inventors: Dino Nisato, St Georges D'Orques; Gérard Le Fur, Montmorency, both of France

[73] Assignee: Sanofi, Paris, France

[21] Appl. No.: 532,652

[22] Filed: Jun. 4, 1990

[30] Foreign Application Priority Data

Jun. 5, 1989 [FR] France .................. 89 07410

[51] Int. Cl.⁵ .............................. A61K 37/00
[52] U.S. Cl. ........................ 514/19; 514/913
[58] Field of Search ................ 514/2, 19, 913

[56] References Cited

U.S. PATENT DOCUMENTS 4,906,613  3/1990  Watkins ........................ 514/16

FOREIGN PATENT DOCUMENTS 211744   2/1987  European Pat. Off. .
0311012  12/1989  European Pat. Off. .

OTHER PUBLICATIONS

Giardina et al., J. Ocular Pharmacology, 6(2), 1990, p. 75.

Primary Examiner—Frederick E. Waddell
Assistant Examiner—Zohreh A. Fay
Attorney, Agent, or Firm—Bacon & Thomas

[57] ABSTRACT

The invention relates to the use of N-(3-pyridylpropionyl)phenylalanylhistidyl (cyclohexyl)statyl-N-(1,3-dihydroxy-2-methylpropyl)isoleucinamide, which has the formula

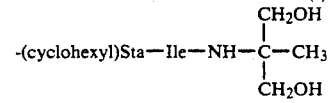

in which: Phe is the (L)-phenylalanine residue, His is the (L)-histidine residue, Ile is the (L)-isoleucine residue and (cyclohexyl)Sta is the cyclohexylstatin residue, i.e. the (3S, 4S)-4-amino-5-cyclohexyl-3-hydroxypentanoic acid residue, for the preparation of drugs useful in the treatment of eye complaints. Application: treatment of eye complaints.

10 Claims, No Drawings

USE OF A STATIN DERIVATIVE IN THE TREATMENT OF EYE COMPLAINTS

The present invention relates to the use of a statin derivative in the treatment of eye complaints such as glaucoma and diabetic retinopathy.

Glaucoma is an eye complaint which is characterized, among other symptoms, by a slow or rapid increase in the intraocular pressure. Glaucoma leads to the destruction of the optic nerve fibers and can result in loss of sight.

One of the major treatments for glaucoma consists in reducing the intraocular pressure. The currently known drugs for the treatment of glaucoma are difficult to use. Thus, for example, pilocarpine has local side-effects, while active principles such as epinephrine or an adrenergic beta-blocker—timolol—are difficult to use on certain patients who suffer from cardiovascular diseases or do not tolerate the general cardiovascular effects of these drugs.

Patent application WO 87/02581 describes the use of certain renin inhibitors for the preparation of drugs intended for reducing and controlling an excessive intraocular pressure.

Diabetic retinopathy is another eye complaint which is generally observed after diabetes has been developing for about fifteen years. It appears in the fundus oculi in the form of microaneurisms and can result in a vascular proliferation, reducing visual acuity.

At the present time, not many treatments exist for combating diabetic retinopathy. An example which may be mentioned is the use of heparin in association with an enzymic fraction of venom.

In certain patients suffering from diabetes mellitus, it has been possible to find an increase in the plasma prorenin level (J. A. Luestscher et al., New England J. Med., 1985, 312 (22), 1412–1417).

The present invention relates to the use of a particularly active renin inhibitor for the preparation of drugs intended for the treatment of eye complaints, especially for controlling the intraocular pressure and for the treatment of ocular hypertension, glaucoma and diabetic retinopathy.

The particularly active renin inhibiting compound whose use forms the subject of the present invention is described in patent application EP 211 744. Said compound is N-(3-pyridylpropionyl)phenylalanylhistidyl(-cyclohexyl)statyl-N-(1,3-dihydroxy-2-methylpropyl-)isoleucinamide, which has the following formula:

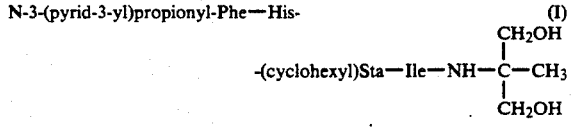

in which: Phe is the (L)-phenylalanine residue, His is the (L)-histidine residue, Ile is the (L)-isoleucine residue and (cyclohexyl)Sta is the cyclohexylstatin residue, i.e. the (3S, 4S)-4-amino-5-cyclohexyl-3-hydroxypentanoic acid residue.

The inhibition of human plasma renin activity at pH 7.4 was measured for this compound (I) according to the method described in patent application EP 211 744. The 50% inhibitory concentration ($IC_{50}$) of compound (I) is $10^{-12}M$.

None of the compounds described in patent application WO 87/02581 has such a high activity as a renin inhibitor.

For the treatment of glaucoma, the invention further relates to the use of compound I in combination with another active principle. The active principle used in combination with compound I can be either an adrenergic beta-blocker, which is itself useful for lowering the intraocular pressure, or an antiinflammatory, especially a steroidal antiinflammatory or a corticosteroid, a side-effect of which is to increase the intraocular pressure.

The present invention further relates to a pharmaceutical composition which contains compound I and which is intended for the treatment of increased intraocular pressure following a treatment with steroidal antiinflammatories.

The pharmaceutical compositions according to the present invention are administered either in the form of ophthalmic pharmaceutical compositions adapted for topical administration to the eye, such as solutions, suspensions or ointments, or in the form of pharmaceutical compositions adapted for systemic administration orally, by injection, percutaneously or by inhalation.

The invention further relates to a combination comprising, on the one hand, compound I in a topical ophthalmic excipient and, on the other hand, an antiinflammatory in a topical ophthalmic excipient for the treatment of glaucoma.

The formulations according to the invention can contain from 0.000001 to 1% by weight of compound I, more particularly from 0.00001 to 0.1%. Each dosage unit comprises an amount of compound I of between 1 ng and 50 mg, preferably of between 5 ng and 25 mg.

The expression "controlling high intraocular pressure", as used in the present description, means regulating, lowering and modulating high intraocular pressure, which is the first symptom enabling glaucoma to be diagnosed. The expression also means that the lowering of the intraocular pressure achieved, according to the invention, by using a compound I is maintained for a sufficient period of time, for example between the administration of 2 consecutive doses.

In the case of the treatment of glaucoma, compound I can be employed in pharmaceutical compositions either as the only active ingredient intended for reducing the intraocular pressure, or in combination with other active principles which are also intended for lowering the intraocular pressure and which act by a different mechanism, such as an adrenergic beta-blocker, for example timolol in the form of the maleate. The utility of a beta-blocker for lowering the intraocular pressure is known. Thus timolol is prescribed in the topical treatment of glaucoma at a rate of one to two drops per day of a solution containing 0.25 mg/100 ml or 0.50 mg/100 ml. It is known, however, that this product must be used with caution because of its activity on the cardiovascular system and its side-effects.

According to one feature of the present invention, it is clear that the use of a compound I in association with a beta-blocker such as timolol maleate can make it possible to reduce the useful dose of beta-blocker and at the same time to observe an equivalent reduction in the intraocular pressure. It will thus be possible to minimize the undesirable effects due to the beta-blocker.

To carry out such a combination treatment, the beta-blocker and compound I are preferably administered together in the form of an ophthalmic composition in a pharmaceutical formulation. The unit dosage form preferably contains:

from 5 μg to 125 μg of adrenergic beta-blocker and from 5 ng to 0.1 mg of compound I.

The amount of each of the active principles can vary according to the severity of the disease and the individual response of the patients.

The concentrations of each of the active principles in the composition making it possible to reduce the intraocular pressure are variable and have a lower limit below which the composition is inactive. This lower limit is about 5% of the effective dose and depends on the age and height of the patient, the severity of the disease and the potency of the beta-blocker used.

The increase in intraocular pressure which is associated with the ophthalmic or systemic use of steroidal antiinflammatories can be reduced by the administration of compound I. Steroidal antiinflammatories include hydrocortisone, cortisone, flunisolide, beclomethasone, alclomethasone, chlorocortolone, diflorasone, alcinolide, fluocinonide, fluocinolone, desoxymethasone, medrysone, paramethasone, 9,21-dichloro-17-(furan-2-yl-carbonyl)oxy-11-hydroxy-16-methyl-α-pregna-1,4-diene-3,20-dione and fluorometholone, as well as their pharmaceutically acceptable salts and esters.

The increase in intraocular pressure can occur following any mode of administration of these drugs: systemic administration, generally orally, or a local injection, for example the injection of a delayed-release form, and particularly a topical or intravitreous ophthalmic injection. Compound I can be administered after the steroid treatment in order to lower the high intraocular pressure or it can be coadministered with the steroid in order to suppress the steroid's effect of increasing the intraocular pressure, without however interfering with its antiinflammatory activity.

According to the present invention, any combination of the dosage forms can be used to administer the combination of antiinflammatory steroid and compound I: both drugs in oral form, or both in topical form, or one in oral form and the other in topical form, or the steroid in the form of a local injection and compound I in topical form; a preferred combination is a topical ophthalmic composition comprising both the steroid and compound I.

The method of reducing and controlling high intraocular pressure, associated with the use of a steroidal antiinflammatory by systemic or ophthalmic administration, also includes the separate administration of this agent and compound I. It is for this reason that the present invention relates to a kit comprising 2 separate units: a pharmaceutical composition comprising compound I and a pharmaceutical composition comprising a steroid. Preferably, such a kit comprises a topical ophthalmic composition of compound I and a pharmaceutical composition of a steroid. Most preferably, the kit comprises two topical ophthalmic compositions, one comprising compound I and the other comprising the steroid. A particular advantage of this presentation is that of providing a composition based on compound I which can be administered once or twice a day, and a composition based on a steroid which can be administered more frequently, for example every hour.

According to the invention, the topical formulation can contain different amounts of active principle, either in the same composition or administered separately.

Compound I represents from 0.000001% to about 1% by weight of the drug, more particularly from 0.00001 to 0.1%. A unit dosage form comprises from 1 ng to 50 mg, preferably between 5 ng and 25 mg. In each individual case, the amount to be administered and the frequency of administration depend on the potency of the chosen steroid, the severity of the eye complaint to be treated and the patient's response.

The steroid represents from 0.05% to about 1.5% by weight of the drug. A unit dosage form comprises from 20 μg to 600 μg to be applied to the eye. In each individual case, the amount to be administered and the frequency of administration depend on the potency of the chosen steroid, the severity of the disease and the patient's response.

According to another feature of the invention, the two active principles, namely compound I and the steroid, are administered simultaneously and are contained in the same pharmaceutical form, each being present in the pharmaceutical form at its preferred concentration. If the steroid is administered systemically or topically, other than ophthalmically, its dosage can vary in accordance with the criteria described above and known to those skilled in the art. As regards the solutions and suspensions, it is also necessary to take account of the volume represented by a drop of pharmaceutical composition.

The intraocular pressure lowering effect of a pharmaceutical composition according to the invention can be determined on animals, for example on rabbits, in a test in which large amounts of water are administered orally, as described for example in Arch. Ophthal., 1969, 82, 381–384 or in J. Ocul. Pharmacol., 1985, 1 (2), 161–168.

Thus compound (I) described in the present patent application was studied for its effect on the intraocular pressure in rabbits. The administration of this compound in the form of an eye lotion enables the intraocular pressure to return rapidly to its normal value after said pressure has been increased by the intravenous injection of a 5% glucose solution.

To prepare suitable formulations, the pharmaceutical compositions can be mixed with a suitable vehicle, either for topical ophthalmic administration or for general administration. As pharmaceutical vehicles acceptable for ophthalmic administration, there may be mentioned water, a mixture of water and water-miscible solvents such as lower alkanols, vegetable oils or mineral oils comprising from 0.5 to 5% by weight of hydroxyethyl cellulose, ethyl oleate, carboxymethyl cellulose, polyvinylpyrrolidone and other non-toxic water-soluble polymers compatible with ophthalmic use, for example cellulose derivatives such as methyl cellulose, an alkali metal derivative of carboxymethyl cellulose, hydroxymethyl cellulose, hydroxyethyl cellulose and hydroxypropylmethyl cellulose, acrylates such as polyacrylic acid salts and ethyl acrylates, polyacrylamides, natural products such as gelatin, alginates, pectins, tragacanth, karaya gum, xanthan gum, carrageenan, agar and acacia, starch derivatives such as starch acetate, hydroxyethyl starch ethers and hydroxypropyl starch, as well as other synthetic derivatives such as polyvinyl alcohol, polyvinylpyrrolidone, polyvinyl methyl ether, polyethylene oxide, neutral carbopol or mixtures of these polymers. The pharmaceutical preparation can also contain non-toxic auxiliary substances such as emulsifiers, preservatives, wetting agents, texturing agents and other substances such as, for example, polyethylene glycols 200, 300, 400 and 600, carbowaxes 1000, 1500, 4000, 6000 and 10,000, antibacterial products such as quaternary ammonium compounds, phenylmercury salts known for having sterilizing properties in the cold without being aggressive, timerosal, propylparaben, benzyl alcohol, phenylethanol, isotonic agents such as an alkali metal chloride, borate, acetate or gluconate buffers, antioxidants such as sodium metabisulfite, butylhydroxyanisole, butylhydroxytoluene or similar agents, and other agents in conventional use, such as sorbitan monolaurate, triethanolamine oleate, polyethylene sorbitan monopalmitate, an alkali metal salt of dioctyl sulfosuccinate, monothioglycerol, ethylenediaminetetraacetic acid or the like.

Furthermore, acceptable ophthalmic excipients can be used, such as, for example, phosphate buffer, isotonic boric acid, an isotonic alkali metal chloride or tris.

The pharmaceutical preparation can also be a suspension in which the particles are water-soluble or water-insoluble polymers. Such a suspension can contain microforms such as microparticles or nanoparticles.

The compositions according to the invention can contain additional therapeutic agents as well as compound I. Thus antibiotics, anesthetics or other agents may be present.

The following Examples illustrate the invention without however limiting it.

EXAMPLE 1

Topical solution
Compound I 1 mg
Sodium chloride 9 mg
Distilled water q.s. 1 ml
1N NaOH q.s. pH=5.5
The constituents of the solution are mixed under the customary conditions to give an ophthalmic solution.

EXAMPLE 2

Topical solution
Compound I 1 mg
Timolol maleate 5 mg
Benzalkonium chloride 0.1 mg
Sodium chloride 9 mg
Distilled water q.s. 1 ml
1N NaOH q.s. pH=5.5
The constituents of the solution are mixed under the customary conditions to give an ophthalmic solution.

What is claimed is:

1. A method of treatment of glaucoma which comprises administering to a subject suffering from glaucoma a drug comprising an effective amount of the compound N-(3-pyridylpropionyl)phenylalanylhistidyl-(cyclohexyl)statyl-N-(1,3-dihydroxy-2-methylpropyl)isoleucinamide.

2. A method according to claim 1 wherein the drug also comprises ophthalmic excipients for topical administration.

3. A method according to claim 1 wherein the drug also comprises pharmaceutical excipients for systemic administration.

4. A method according to claim 1 wherein the effective amount is 0.000001 to 1% by weight of the compound.

5. A method according to claim 4 wherein the effective amount is 0.00001 to 0.1% by weight of the compound.

6. A method of treatment of diabetic retinopathy which comprises administering to a subject suffering from glaucoma a drug comprising an effective amount of the compound N-(3-pyridylpropionyl)phenylalanylhistidyl-(cyclohexyl)statyl-N-(1,3-dihydroxy-2-methylpropyl)isoleucinamide.

7. A method according to claim 6 wherein the drug also comprises ophthalmic excipients for topical administration.

8. A method according to claim 6 wherein the drug also comprises pharmaceutical excipients for systemic administration.

9. A method according to claim 6 wherein the effective amount is 0.000001 to 1% by weight of the compound.

10. A method according to claim 9 wherein the effective amount is 0.00001 to 0.1% by weight of the compound.

* * * * *

UNITED STATES PATENT AND TRADEMARK OFFICE
CERTIFICATE OF CORRECTION

PATENT NO. : 5,134,124

DATED : July 28, 1992

INVENTOR(S) : NISATO et al.

It is certified that error appears in the above-identified patent and that said Letters Patent is hereby corrected as shown below:

Column 6, claim 6, line 3, delete "glaucoma" and insert —diabetic retinopathy—.

Signed and Sealed this

Twenty-ninth Day of March, 1994

Attest:

BRUCE LEHMAN

*Attesting Officer*     *Commissioner of Patents and Trademarks*